United States Patent
Lock

(10) Patent No.: US 7,534,812 B2
(45) Date of Patent: May 19, 2009

(54) PROCESS FOR PREPARATION OF ISOCHROMAN AND DERIVATIVES THEREOF

(75) Inventor: Ralf Lock, Mainz (DE)

(73) Assignee: Boehringer Ingelheim Pharma GmbH & Co. KG, Ingelheim (DE)

( * ) Notice: Subject to any disclaimer, the term of this patent is extended or adjusted under 35 U.S.C. 154(b) by 52 days.

(21) Appl. No.: 11/275,731

(22) Filed: Jan. 26, 2006

(65) Prior Publication Data

US 2006/0173196 A1 Aug. 3, 2006

(30) Foreign Application Priority Data

Jan. 28, 2005 (DE) .................. 10 2005 004021
Feb. 8, 2005 (DE) .................. 10 2005 005620

(51) Int. Cl.
*A01N 43/16* (2006.01)
*C07D 307/77* (2006.01)

(52) U.S. Cl. .................. 514/456; 549/240

(58) Field of Classification Search .......... 514/456; 549/240
See application file for complete search history.

(56) References Cited

U.S. PATENT DOCUMENTS

| | | | |
|---|---|---|---|
| 4,021,558 A * | 5/1977 | Kutter et al. | 514/309 |
| 4,031,219 A | 6/1977 | Kutter et al. | |
| 5,116,739 A | 5/1992 | Teranishi et al. | |
| 6,652,860 B1 | 11/2003 | Singh et al. | |
| 6,818,774 B2 * | 11/2004 | Cesura et al. | 546/196 |

FOREIGN PATENT DOCUMENTS

DE 2000339 A1 7/1971

WO WO 99/31227 6/1999

OTHER PUBLICATIONS

Goo-On et al J. Org. Chem. 1954, 19, 305-311.*
De Silva et al Canadian J. Chem. 1979, 57, 1598-1605.*
Cameron et al Tet. Lett. 1993, 34, 4689-4692.*
Hunt, Donald F. et al., "Peptides Presented to the Immune System by Murine Class II Major Histocompatibility Complex Molecule I-Ad," Science, vol. 256, pp. 1817-1820, Jun. 26, 1992.
von Rohr, A. et al., "Clinical Applications of Interleukin-2," Progress in Growth Factor Research, vol. 4, pp. 229-246, 1992.
Rider, Beverley J. et al., "Immune Responses to Self Peptides Naturally Presented by Murine Class II Major Histocompatibility Complex Molecules," Molecular Immunology, vol. 33, No. 7/8., pp. 625-633, 1996.
International Search Report for PCT/CA 98/01129 dated Jun. 17, 1999.
International Search Report, Form PTC/ISA/220, for corresponding PCT/EP2006/050401.

* cited by examiner

*Primary Examiner*—Rita J Desai
*Assistant Examiner*—John Mabry
(74) *Attorney, Agent, or Firm*—Michael P. Morris; Mary-Ellen M. Devlin; Philip I. Datlow

(57) ABSTRACT

The present invention relates to an improved process for preparing compounds of formula 1 on an industrial scale,

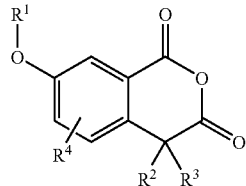

wherein $R^1$, $R^2$ and $R^3$ are independently $C_{1-6}$-alkyl, $C_{2-6}$-alkenyl, $C_{2-6}$-alkynyl or aryl; and $R^4$ is H, $OC_{1-6}$-alkyl, Oaryl, OH, $C_{1-6}$-alkyl, halogen, CN or $NO_2$.

15 Claims, No Drawings

PROCESS FOR PREPARATION OF ISOCHROMAN AND DERIVATIVES THEREOF

FIELD OF THE INVENTION

The present invention relates to a process for preparing isochroman and derivatives thereof. Isochroman and derivatives thereof have a general formula 1:

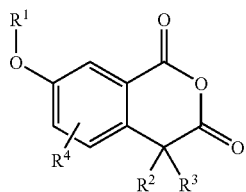

wherein $R^1$, $R^2$ and $R^3$ each independently represent $C_{1-6}$-alkyl, $C_{2-6}$-alkenyl, $C_{2-6}$-alkynyl or aryl, and $R^4$ represents H, $OC_{1-6}$-alkyl, Oaryl, OH, $C_{1-6}$-alkyl, halogen, CN or $NO_2$. In particular, these compounds are valuable intermediate products for the synthesis of pharmaceutically active substances, for example, gliquidone or glurenorm, which are commercially important pharmaceutical agents for the treatment of age-related diabetes.

DESCRIPTION OF THE INVENTION

Terms and Definitions

All terms as used herein, unless otherwise stated, shall be understood in their ordinary meaning as known in the art. The term "$C_{1-6}$-alkyl" (including those which are part of other groups) refers to both branched and unbranched alkyl groups containing 1 to 6 carbon atoms, and the term "$C_{1-4}$-alkyl" refers to both branched and unbranched chains containing 1 to 4 carbon atoms. Alkyl groups with 1 to 4 carbon atoms are preferred. Examples of $C_{1-6}$-alkyl include methyl, ethyl, n-propyl, iso-propyl, n-butyl, iso-butyl, sec-butyl, tert-butyl, n-pentyl, iso-pentyl, neo-pentyl or hexyl. The following abbreviations may optionally be used for the above-mentioned groups: Me, Et, n-Pr, i-Pr, n-Bu, i-Bu, s-Bu, t-Bu, and so on. Unless stated otherwise, the definitions propyl, butyl, pentyl and hexyl include all the possible isomeric forms of the groups. For example, propyl includes n-propyl and iso-propyl, butyl includes iso-butyl, sec-butyl and tert-butyl, and so on.

The term "$C_{2-6}$-alkenyl" (including those which are part of other groups) refers to branched and unbranched alkenyl groups with 2 to 6 carbon atoms and the term "$C_{2-4}$-alkenyl" refers to branched and unbranched alkenyl groups with 2 to 4 carbon atoms, provided that they have at least one double bond. Alkenyl groups with 2 to 4 carbon atoms are preferred. Examples include ethenyl or vinyl, propenyl, butenyl, pentenyl or hexenyl. Unless stated otherwise, the definitions propenyl, butenyl, pentenyl and hexenyl include all the possible isomeric forms of the groups in question. For example, propenyl includes 1-propenyl and 2-propenyl, butenyl includes 1-, 2- and 3-butenyl, 1-methyl-1-propenyl, 1-methyl-2-propenyl, and so on.

The term "$C_{2-6}$-alkynyl" (including those which are part of other groups) refers to branched and unbranched alkynyl groups with 2 to 6 carbon atoms and the term "$C_{2-4}$-alkynyl" refers to branched and unbranched alkynyl groups with 2 to 4 carbon atoms, provided that they have at least one triple bond. Alkynyl groups with 2 to 4 carbon atoms are preferred. Examples include ethynyl, propynyl, butynyl, pentynyl, or hexynyl. Unless stated otherwise, the definitions propynyl, butynyl, pentynyl and hexynyl include all the possible isomeric forms of the groups in question. For example, propynyl includes 1-propynyl and 2-propynyl, butynyl includes 1,2- and 3-butynyl, 1-methyl-1-propynyl, 1-methyl-2-propynyl, and so on.

The term "aryl" (including those which are part of other groups) refers to aromatic ring systems with 6 or 10 carbon atoms. Examples include phenyl or naphthyl, preferably phenyl. Unless otherwise stated, the aromatic groups may be substituted by one or more groups selected from the group consisting of methyl, ethyl, iso-propyl, tert-butyl, hydroxy, fluorine, chlorine, bromine and iodine.

Halogen as defined herein refers to fluorine, chlorine, bromine or iodine. Unless otherwise stated, fluorine, chlorine and bromine are preferred halogens.

According to the present invention, the term "acid" refers to a proton donor. The acid may be introduced into a reaction solution as an aqueous solution of varying concentrations or in pure form (gaseous, liquid or solid). Inorganic acids, in concentrated or dilute aqueous solution, are preferred and include HCl, $HNO_3$, $H_2SO_4$, $H_2CO_3$ or $H_3PO_4$.

The term "Lewis acid" refers to an electron pair acceptor, preferably a neutral compound with an electron deficiency. Examples include $B(CH_3)_3$, $BF_3$, $SO_3$, $AlCl_3$, $SiCl_4$ or $PF_5$.

As used herein, the term "solvent" refers to an organic, low-molecular weight substance that can dissolve other organic substances physically. In accordance with this invention, a prerequisite for solvent suitability is that neither the dissolving nor the dissolved substance changes chemically during the dissolution process, i.e., that the components of the solution can be recovered in their original form by physical separation processes such as distillation, crystallization, sublimation, evaporation, adsorption. Not only pure solvents, but also mixtures of solvents that combine solvating properties may be used. Examples include alcohols, preferably methanol, ethanol, propanols, butanols, octanols, cyclohexanol; glycols, preferably ethyleneglycol, diethyleneglycol; ethers/glycolethers, preferably diethyl ether, dibutylether, anisole, dioxane, tetrahydrofuran, mono-, di-, tri-, polyethyleneglycolether; ketones, preferably acetone, butanone, cyclohexanone; esters, preferably acetic acid esters, glycol esters; amides, inter alia nitrogen compounds, preferably dimethylformamide, pyridine, N-methylpyrrolidone, acetonitrile; sulfur compounds, preferably carbon disulfide, dimethylsulfoxide, sulfolane; nitro compounds, preferably nitrobenzene; halohydrocarbons, preferably dichloromethane, chloroform, tetrachloromethane, tri-, tetrachloroethene, 1,2-dichloroethane, chlorofluorocarbons; aliphatic or alicyclic hydrocarbons, preferably benzene or petroleum ether, cyclohexane, methylcyclohexane, decalin, terpene-L; aromatic hydrocarbons, preferably benzene, toluene, xylenes; and mixtures thereof.

In a preferred embodiment of this invention, the solvent may be selected from the group consisting of: alcohols, preferably methanol, ethanol, propanols, butanols; ethers, preferably diethyl ether, dibutylether, tetrahydrofuran; ketones, preferably acetone, butanone, cyclohexanone; esters, preferably acetic acid esters; halohydrocarbons, preferably dichloromethane, chloroform, trichloroethene, tetrachloroethene, 1,2-dichloroethane; aromatic hydrocarbons, preferably benzene, toluene, xylenes; and mixtures thereof. In a more preferred embodiment, the solvent is methanol, ethanol, propanols, butanols, diethyl ether, dibutylether, tetrahydrofuran, acetone, cyclohexanone, acetic acid esters, dichloromethane, chloroform, 1,2-dichloroethane, toluene, xylenes or mixtures thereof.

The term "$C_{1-8}$-alcohol" refers to branched and unbranched alcohols with 1 to 8 carbon atoms and one or two hydroxy groups. Accordingly, the term "$C_{1-4}$-alcohol" refers to branched and unbranched alkyl groups with 1 to 4 carbon atoms and one or two hydroxy groups. Preferably, alcohols according to this invention comprise 1 to 4 carbon atoms. Examples of $C_{1-8}$-alcohols include: methanol, ethanol, n-propanol, iso-propanol, n-butanol, iso-butanol, sec-butanol, tert-butanol, n-pentanol, iso-pentanol, neo-pentanol or hexanol. The abbreviations MeOH, EtOH, n-PrOH, i-PrOH, n-BuOH, i-BuOH, t-BuOH, and so on, may optionally be used for the above-mentioned molecules. Unless stated otherwise, the definitions propanol, butanol, pentanol and hexanol include all the possible isomeric forms of the groups in question. Thus, for example, propanol includes n-propanol and iso-propanol, butanol includes iso-butanol, sec-butanol and tert-butanol etc.

The term "solution of strong base" refers to a solution preferably prepared with water and 25-75 wt % of a base. The base used may be an organic base or inorganic base, e.g., in the form of an aqueous solution. Examples of inorganic bases include alkali metal salts or alkali metal hydroxides. Preferably, alkali metal hydroxides are used. and In a more preferred embodiment, $Na_2CO_3$, $K_2CO_3$, LiOH, NaOH, KOH or $NaHCO_3$, is used. Suitable organic bases include tertiary amines, preferably tertiary alkylamines, tertiary alkyl-arylamines or pyridines. In a preferred embodiment, trialkylamines with branched or unbranched $C_{1-6}$-alkyl groups are used. For example, triethylamine or diisopropylethylamine is preferred. The reaction may optionally also be carried out in the presence of basic polymers with, e.g., tertiary amino functions.

Process for Preparation of Isochroman and Derivatives Thereof

This invention relates to a process for preparing a compound of formula 1,

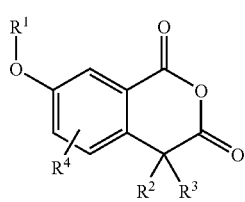

wherein:

$R^1$, $R^2$ and $R^3$ are independently $C_{1-6}$-alkyl, $C_{2-6}$-alkenyl, $C_{2-6}$-alkynyl or aryl; and $R^4$ is H, $OC_{1-6}$-alkyl, Oaryl, OH, $C_{1-6}$-alkyl, halogen, CN or $NO_2$, and said process comprises:

a) treating an acrylic acid derivative of formula 4 with an HBr solution to form a mixture and reacting the mixture with a compound of formula 5 in the presence of aluminum chloride to form compound of formula 3;

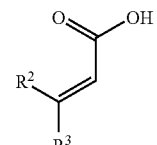

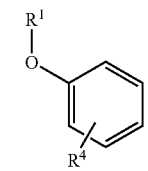

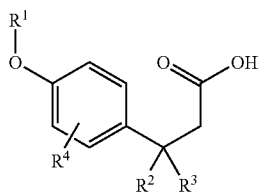

b) optionally converting the compound of formula 3 produced in step a) into an acid halide or an anhydride;

c) treating the compound of formula 3 with a Lewis acid followed by reacting the compound of formula 3 with a $C_{1-6}$-alkyl nitrite to form a compound of formula 2; and

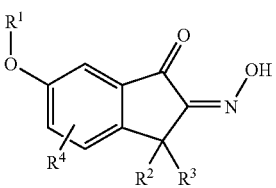

d) reacting the compound of formula 2 in the presence of a base with a sulfonic acid halide, saponifying followed by hydrolyzing to form the compound of formula 1, wherein $R^1$-$R^4$ of compounds of formulas 2-5 are as defined above.

In one embodiment of this invention, the Lewis acid is selected from the group consisting of polyphophoric acid, a mixture of phosphorus pentoxide and methanesulfonic acid, bismuth triflate, lanthanide triflate and bistrifluoromethanesulfonylimide. In another embodiment, the sulfonic acid halide is toluenesulfonic acid chloride.

In a preferred embodiment, $R^1$, $R^2$ and $R^3$ are independently $C_{1-6}$-alkyl, more preferably $C_{1-4}$-alkyl. In a more preferred embodiment, $R^1$, $R^2$ and $R^3$ are independently methyl, ethyl, iso-propyl or tert-butyl. In a most preferred embodiment, $R^1$, $R^2$ and $R^3$ represent methyl groups.

In another preferred embodiment, $R^4$ is H, $C_{1-6}$-alkyl, halogen, CN or $NO_2$. In yet another preferred embodiment, $R^4$ is H, methyl, ethyl, iso-propyl or tert-butyl. In a more preferred embodiment, $R^4$ is H.

In a preferred embodiment, process step a) comprises i) treating the acrylic acid of formula 4 with between about 40% and about 80% HBr solution; ii) stirring the mixture for between about 20 minutes and about 100 minutes at a temperature of between about 0° C. and about 50° C.; iii) extracting the mixture with a solvent; iv) eliminating the solvent either substantially or totally from the mixture, wherein an intermediate product is formed; v) dissolving the intermediate product in a compound of formula 5 with or without an additional solvent; vi) adding said aluminum chloride followed by stirring for between about 2 and about 6 hours at a temperature of between about 0° C. and about 50° C. until reaction is complete; and vii) purifying resultant product by extraction and recrystallization.

In another preferred embodiment, process step a) comprises i) treating the acrylic acid derivative of formula 4 with between about 60% and about 65% HBr solution; ii) stuffing said mixture for between about 25 minutes and about 70 minutes at a temperature of between about 20° C. and about 35° C.; iii) extracting said mixture with an aromatic solvent; iv) eliminating said solvent either substantially or totally from said mixture, wherein an intermediate product is formed; v) dissolving said intermediate product in a compound of formula 5; vi) adding said aluminum chloride followed by stirring for between about 3 hours and about 5 hours at a temperature of between about 20° C. and about 30° C.; vii) adding water to terminate reaction, wherein an organic phase and an aqueous phase is formed; viii) extracting a product from the organic phase with a solution of strong base; ix) eliminating organic-phase solvent substantially or totally from the product; and x) recrystallizing the product from an aliphatic hydrocarbon. Optionally, after step viii) and before step ix), the process above further comprises acidifying the solution and extracting the product with an additional solvent from the solution.

In a preferred embodiment, process step c) comprises i) treating compound 3 with a Lewis acid to form a mixture; ii) heating the mixture for between about 10 minutes to about 50 minutes at a temperature of between about 50° C. and about 90° C.; iii) extracting the mixture into an organic phase with a solvent; iv) washing the organic phase; v) eliminating the solvent substantially or totally from the mixture to form a residue; vi) dissolving the residue in an alcohol and combining with concentrated hydrochloric acid; vii) adding the $C_{1-6}$-alkyl nitrite and stirring for between about 30 minutes and about 90 minutes at a temperature of between about 30° C. and 70° C. to form a solid; and viii) filtering and washing the solid. Preferably, the Lewis acid is polyphosphoric acid. Preferably, the solvent in step iii) is an ether, ester, halohydrocarbon or aromatic hydrocarbon. Preferably, the $C_{1-6}$-alkyl nitrite in step vii) is isoamyl nitrite.

In another preferred embodiment, process step c) comprises i) treating compound 3 with a Lewis acid to form a mixture; ii) heating the mixture for between about 20 minutes to about 40 minutes at a temperature of between about 60° C. and about 80° C.; iii) adding water to the mixture; iv) extracting the mixture into an organic phase with a solvent; v) washing the organic phase with a solution of a strong base at pH between about 8.5 and about 9.5; vi) washing the organic phase with a dilute hydrochloric acid solution; vii) eliminating the solvent substantially or totally from the mixture to form a residue; viii) dissolving the residue in an alcohol and combining with concentrated hydrochloric acid; ix) adding the $C_{1-6}$-alkyl nitrite and stirring for between about 50 minutes and about 70 minutes at a temperature of between about 40° C. and 60° C. to form a solid; and x) filtering and washing said solid. Preferably, the Lewis acid is polyphosphoric acid. Preferably, the solvent in step iv) is an aromatic solvent. Preferably, the $C_{1-6}$-alkyl nitrite in step ix) is isoamyl nitrite.

In a preferred embodiment, process step d) comprises i) suspending compound 2 in water to form a mixture; ii) adding a solution of a strong base to the mixture; iii) heating the mixture to a temperature between about 30° C. and about 70° C.; iv) adding benzenesulfonyl chloride to the mixture; v) stirring the mixture for between about 30 minutes and about 90 minutes; vi) washing the mixture with a solvent; vii) acidifying the mixture with an acid; viii) extracting the mixture with an aromatic solvent; (ix) eliminating the solvent substantially or totally from the mixture; x) recrystallizing the mixture from a $C_{1-8}$-alcohol. Preferably, the solvent in step vi) is an aromatic solvent.

In another preferred embodiment, process step d) comprises i) suspending compound 2 in water to form a mixture; ii) adding a solution of a strong base to the mixture; iii) heating the mixture to a temperature between about 40° C. and about 60° C.; iv) adding benzenesulfonyl chloride to the mixture; v) stirring said mixture for between about 50 minutes and about 70 minutes; vi) washing said mixture with a solvent; vii) acidifying said mixture with concentrated hydrochloric acid; viii) extracting said mixture with an aromatic solvent; ix) eliminating said solvent substantially or totally from said mixture; x) recrystallizing said mixture from a $C_{1-8}$-alcohol. Preferably, the solvent in step vi) is an aromatic solvent.

In yet another preferred embodiment, this invention relates to a process for preparing isochroman of formula 1A,

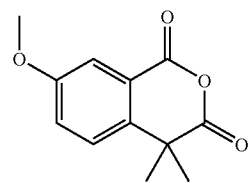

1A said process comprising:

a) mixing 3,3-dimethylacrylic acid with stirring with an excess of 62% hydrobromic acid at 30-50° C.; stirring for 50-70 minutes at 15-40° C.; extracting with toluene; evaporating to dryness in vacuo; dissolving the crude product in an excess of anisole; adding the mixture to anisole and the 1-2-fold molar excess of aluminum chloride, based on the 3,3-dimethylacrylic acid; stirring for 3-5 hours at ambient temperature; adding the solution to an excess of ice water; stirring for 70-90 minutes; extracting the organic phase at 50-60° C. with 62% hydrobromic acid, with 1-2M sodium hydroxide solution, extracting this sodium hydroxide solution phase twice with toluene and then acidifying with hydrobromic acid and twice more with toluene; evaporating the organic phase to dryness; recrystallizing the residue from methylcyclohexane; drying the residue in vacuo at 40-60° C.;

b) reacting the compound 3A obtained in step a) by adding the compound 3 to an excess of polyphosphoric acid; heating the mixture to 60-80° C.; stirring the mixture for 20-40 minutes; cooling to 40-60° C.; adding an excess of water while cooling; extracting the mixture with toluene; washing with sodium hydroxide solution at pH 8.5-9.5; extracting the aqueous phase with toluene; washing the combined toluene phases with dilute hydrochloric acid; evaporating in vacuo; dissolving the residue in an excess of a mixture of 4.5 to 5.5 parts by volume of methanol and one part by volume of conc. hydrochloric acid; heating to 40-60° C.; adding a 2.5 to 3-fold molar excess of isoamyl nitrite, based on the compound of formula 3; stirring for 50-70 minutes at 40-60° C.; cooling and filtering the solid; washing with methanol; drying the residue in vacuo at 40-60° C.; and

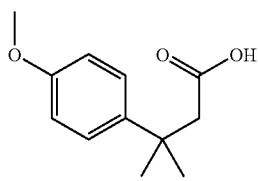

c) reacting the compound 2A obtained in step b), by suspending the compound 2 in water; adding a 2-20-fold molar excess of 45% sodium hydroxide solution, based on 2; heating the solution to 40-60° C.; adding a 1- to 2-fold molar excess of benzenesulfonyl chloride, based on 2, optionally dissolved in toluene; stirring the mixture for 50-70 min; washing the aqueous phase with toluene; acidifying with conc. hydrochloric acid; washing the aqueous phase with toluene; evaporating the organic phase to dryness; recrystallizing the residue from isopropanol

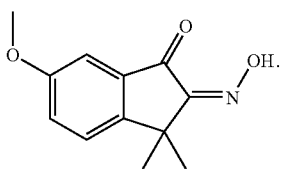

In another embodiment, the present invention relates to compounds of formula 1 prepared according to any one of the processes defined above.

In order that this invention be more fully understood, the following examples of the inventive process are set forth. These examples are for the purpose of illustration only and are not to be construed as limiting the scope of the invention in any way.

EXAMPLES

Example 1

Compound 3A

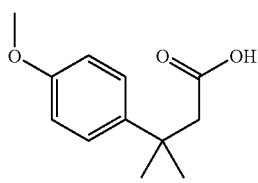

250 g of 3,3-dimethylacrylic acid are added to 1 L 62% hydrobromic acid (HBr) at 20° C. with stirring. The mixture is stirred for 60 minutes at 20° C.-35° C., then extracted at 35° C. with 900 mL of toluene in several batches. The combined organic extracts are evaporated to dryness in vacuo. 417 g (92%) crude product are obtained. 408 g of the crude product are dissolved in 660 mL anisole and 70 mL solvent are distilled off in vacuo. The solution at a temperature of 35° C. is added to a mixture of 1 L anisole and 442.4 g aluminum chloride kept at a temperature of 20° C. The mixture is stirred for 4 hours at ambient temperature, then the solution is poured into 1.5 L of ice water and stirred for 80 minutes. The phases are separated and the organic phase is extracted with 250 mL of 62% hydrobromic acid. Then the organic phase is extracted with 1.5 L of sodium hydroxide solution at pH 10-11. After the phase separation the aqueous phase is washed twice more with 350 mL of toluene. The aqueous phase is adjusted to pH 1-2 with hydrobromic acid at 50-60° C. and extracted with 1.25 L toluene in 2 batches. These toluene phases are evaporated to dryness in vacuo and the residue is crystallized with 510 mL methylcyclohexane at 5° C. The solid obtained is separated off, washed with 100 mL methylcyclohexane and dried in vacuo at 50° C. Yield 149.8 g (32%) of compound 3A.

Example 2

Compound 2A

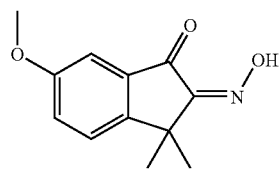

222 g of compound 3A are added to 1.11 kg polyphosphoric acid. The mixture is heated to 70° C. and stirred for 30 minutes at this temperature. After cooling to 50° C., 1.1 L of water is added while cooling. The resulting solution is extracted with 430 mL of toluene. Then the toluene phase is washed with 220 mL sodium hydroxide solution at pH 9 and the aqueous phase is extracted with 80 mL of toluene. The combined toluene phases are washed with 120 mL dilute hydrochloric acid at about pH 3 and then evaporated down in vacuo. The residue remaining is dissolved in 650 mL of methanol and combined with 125 mL of conc. hydrochloric acid. The mixture is heated to 50° C., 326 g isoamyl nitrite is added batchwise and the mixture is stirred for 1 hour at 50° C. After cooling to 20° C. the solid obtained is filtered off, washed with 240 mL of methanol and dried in vacuo at 50° C. Yield 142 g (61%) of compound 2A.

Example 3

Compound 1A

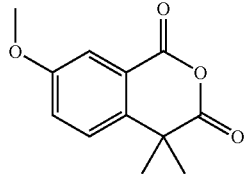

82 g of 2A are added to 370 mL of water. 75 mL of 45% sodium hydroxide solution are added and the solution is heated to 50° C. Then a solution of 72.7 g benzenesulfonyl chloride in 290 mL of toluene is added dropwise with stirring and the mixture is stirred for 1 hour at 50° C. Then the phases are separated and the aqueous phase is washed twice with 140 mL of toluene. Then it is acidified with 90 mL of conc.

hydrochloric acid and stirred for 10 minutes. Then the aqueous phase is extracted with 300 mL and with 150 mL of toluene. The toluene phases are combined and evaporated to dryness in vacuo. The residue is taken up in 360 mL isopropanol at boiling point and crystallized after cooling to 20° C. The solid obtained is separated off and dried in vacuo at 50° C. Yield 68 g (83%) of compound 1A.

I claim:

1. A process for preparing a compound of formula 1,

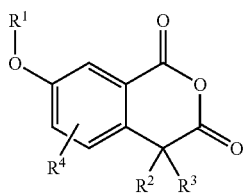

wherein:
$R^1$, $R^2$ and $R^3$ are independently $C_{1-6}$-alkyl, $C_{2-6}$-alkenyl, $C_{2-6}$-alkynyl or aryl; and
$R^4$ is H, $OC_{1-6}$-alkyl, Oaryl, OH, $C_{1-6}$-alkyl, halogen, CN or $NO_2$; comprising the steps of:

a) treating an acrylic acid compound of formula 4 with an HBr solution to form a mixture and reacting the mixture with a compound of formula 5 in the presence of aluminum chloride to form a compound of formula 3;

b) optionally converting the compound of formula 3 produced in step a) into an acid halide or an anhydride;

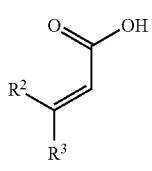

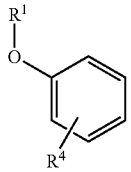

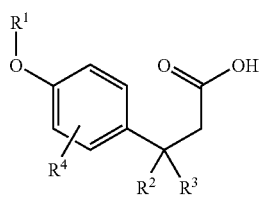

c) treating the compound of formula 3, or the acid halide or anhydride thereof, with a Lewis acid followed by reacting the compound of formula 3 with a $C_{1-6}$-alkyl nitrite to form a compound of formula 2; and

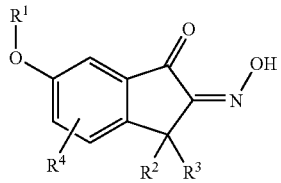

d) reacting the compound of formula 2 in the presence of a base with a sulfonic acid halide, saponifying followed by hydrolyzing to form the compound of formula 1, wherein $R^1$-$R^4$ of compounds of formulas 2-5 are as defined above.

2. The process according to claim 1, wherein the Lewis acid is selected from the group consisting of: polyphosphoric acid, a mixture of phosphorus pentoxide and methanesulfonic acid, bismuth triflate, lanthanide triflate and bistrifluoromethanesulfonylimide.

3. The process according to claim 1, wherein the sulfonic acid halide is toluenesulfonic acid chloride.

4. The process according to claim 1, wherein $R^1$, $R^2$ and $R^3$ are independently $C_{1-6}$-alkyl.

5. The process according to claim 4, wherein $R^1$, $R^2$ and $R^3$ are independently methyl, ethyl, iso-propyl or tert-butyl.

6. The process according to claim 1, wherein $R^4$ is H, $C_{1-6}$-alkyl, halogen, CN or $NO_2$.

7. The process according to claim 1, wherein $R^4$ is H, methyl, ethyl, iso-propyl or tert-butyl.

8. The process according to claim 1, wherein step a) comprises:
 i) treating compound 4 with between about 40% and about 80% HBr solution;
 ii) stirring said mixture for between about 20 minutes and about 100 minutes at a temperature of between about 0° C. and about 50° C.;
 iii) extracting said mixture with a solvent;
 iv) eliminating said solvent either substantially or totally from said mixture, wherein an intermediate product is formed;
 v) dissolving said intermediate product in compound 5 with or without an additional solvent;
 vi) adding said aluminum chloride followed by stuffing for between about 2 hours and about 6 hours at a temperature of between about 0° C. and about 50° C. until reaction is complete; and
 vii) purifying compound 3 by extraction and recrystallization.

9. The process according to claim 1, wherein step a) comprises:
 i) treating compound 4 with between about 60% and about 65% HBr solution;
 ii) stirring said mixture for between about 250 minutes and about 70 minutes at a temperature of between about 20° C. and about 35° C.;
 iii) extracting said mixture with an aromatic solvent;
 iv) eliminating said solvent either substantially or totally from said mixture, wherein an intermediate product is formed;
 v) dissolving said intermediate product in compound 5;
 vi) adding said aluminum chloride and stirring said mixture for between about 3 hours and about 5 hours at a temperature of between about 20° C. and about 30° C.;

vii) adding water to said mixture to terminate reaction, wherein an organic phase and an aqueous phase is formed;
viii) extracting a product from the organic phase with a solution of strong base;
ix) acidifying said solution;
x) extracting compound 3 with an additional solvent from said solution;
xi) eliminating said additional solvent substantially or totally; and
xii) recrystallizing compound 3 from an aliphatic hydrocarbon.

10. The process according to claim 1, wherein step c) comprises:
   i) treating compound 3, or the acid halide or anhydride thereof, with a Lewis acid to form a mixture, wherein the Lewis acid is polyphosphoric acid;
   ii) heating said mixture for between about 10 minutes to about 50 minutes at a temperature of between about 50° C. and about 90° C.;
   iii) extracting said mixture into an organic phase with a solvent;
   iv) washing said organic phase;
   v) eliminating said solvent substantially or totally from said mixture to form a residue;
   vi) dissolving said residue in an alcohol and adding concentrated hydrochloric acid;
   vii) adding said $C_{1-6}$-alkyl nitrite and stirring for between about 30 minutes and 90 minutes at a temperature of between about 30° C. and 70° C. to form a solid of compound 2; and
   viii) filtering and washing said solid.

11. The process according to claim 10, wherein in step i) the Lewis acid is polyphosphoric acid, in step iii) the solvent is selected from the group consisting of ether, ester, halohydrocarbon and aromatic hydrocarbon and in step vii) the $C_{1-6}$-alkyl nitrite is isoamyl nitrate.

12. The process according to claim 1, wherein step c) comprises:
   i) treating compound 3, or the acid halide or anhydride thereof, with a Lewis acid to form a mixture, wherein the Lewis acid is polyphosphoric acid;
   ii) heating said mixture for between about 20 minutes to about 40 minutes at a temperature of between about 60° C. and about 80° C.;
   iii) adding water to said mixture;
   iv) extracting said mixture into an organic phase with a solvent;
   v) washing said organic phase with a solution of a strong base at pH between about 8.5 and about 9.5;
   vi) washing said organic phase with a dilute hydrochloric acid solution;
   vii) eliminating said solvent substantially or totally from said mixture to form a residue;
   viii) dissolving said residue in an alcohol and adding concentrated hydrochloric acid;
   ix) adding said $C_{1-6}$-alkyl nitrite and stirring for between about 50 minutes and about 70 minutes at a temperature of between about 40° C. and 60° C. to form a solid of compound 2, wherein said $C_{1-6}$-alkyl nitrite is isoamyl nitrate; and
   x) filtering and washing said solid.

13. The process according to claim 12, wherein in step i) the Lewis acid is polyphosphoric acid, in step iv) the solvent is an aromatic solvent and in step ix) the $C_{1-6}$-alkyl nitrite is isoamyl nitrate.

14. The process according to claim 1, wherein step d) comprises:
   i) suspending compound 2 in water to form a mixture;
   ii) adding a solution of a strong base to said mixture;
   iii) heating said mixture to a temperature between about 30° C. and about 70° C.;
   iv) adding benzenesulfonyl chloride to said mixture;
   v) stirring said mixture for between about 30 minutes and about 90 minutes;
   vi) washing said mixture with an aromatic solvent;
   vii) acidifying said mixture with an acid;
   viii) extracting said mixture with an aromatic solvent;
   ix) eliminating said solvent substantially or totally from said mixture to form a residue of compound 1; and
   x) recrystallizing said residue from a $C_{1-8}$-alcohol.

15. The process according to claim 1, wherein step d) comprises:
   i) suspending compound 2 in water to form a mixture;
   ii) adding a solution of a strong base to said mixture;
   iii) heating said mixture to a temperature between about 40° C. and about 60° C.;
   iv) adding benzenesulfonyl chloride to said mixture;
   v) stirring said mixture for between about 50 minutes and about 70 minutes;
   vi) washing said mixture with an aromatic solvent;
   vii) acidifying said mixture with concentrated hydrochloric acid;
   viii) extracting said mixture with an aromatic solvent;
   ix) eliminating said solvent substantially or totally from said mixture to form a residue of compound 1; and
   x) recrystallizing said residue from a $C_{1-8}$-alcohol.

* * * * *